United States Patent [19]

Lerner

[11] Patent Number: 5,522,386
[45] Date of Patent: Jun. 4, 1996

[54] APPARATUS PARTICULARLY FOR USE IN THE DETERMINATION OF THE CONDITION OF THE VEGETATIVE PART OF THE NERVOUS SYSTEM

[76] Inventor: Eduard N. Lerner, Ernststraat 17, NL-1083 GP Amsterdam, Netherlands

[21] Appl. No.: 140,056

[22] PCT Filed: Apr. 29, 1992

[86] PCT No.: PCT/NL92/00079

§ 371 Date: Nov. 24, 1993

§ 102(e) Date: Nov. 24, 1993

[87] PCT Pub. No.: WO92/19192

PCT Pub. Date: Nov. 12, 1992

[30] Foreign Application Priority Data

Apr. 29, 1991 [NL] Netherlands ............ 9100740

[51] Int. Cl.[6] ................................. A61B 5/00
[52] U.S. Cl. ................ 128/630; 128/745; 128/746; 128/744; 128/741
[58] Field of Search .................. 128/731–4, 736, 128/739–42, 744, 745–6

[56] References Cited

U.S. PATENT DOCUMENTS

| | | | |
|---|---|---|---|
| 3,837,331 | 9/1974 | Ross | 128/732 X |
| 3,893,450 | 7/1975 | Ertl | 128/731 |
| 4,131,113 | 12/1978 | Fender et al. | |
| 4,201,224 | 5/1980 | John | |
| 4,462,411 | 7/1984 | Rickards | 128/731 X |
| 4,557,271 | 12/1985 | Stoller et al. | |
| 4,561,449 | 12/1985 | Hu et al. | |
| 4,570,640 | 2/1986 | Barsa | |
| 4,987,903 | 1/1991 | Keppel et al. | 128/731 X |
| 5,036,858 | 8/1991 | Carter et al. | 128/732 |
| 5,191,894 | 3/1993 | Yasushi | 128/733 |
| 5,291,894 | 3/1994 | Nagy | 128/732 X |
| 5,331,969 | 7/1994 | Silberstein | 128/731 |

FOREIGN PATENT DOCUMENTS

| | | |
|---|---|---|
| 0208007 | 1/1987 | European Pat. Off. |
| 2113846 | 8/1983 | United Kingdom. |
| WO90/14794 | 12/1990 | WIPO. |

OTHER PUBLICATIONS

By Y. Kosugi et al., "Quantitive Evaluation of Saccadic Eye Movement Disorders Under Random Visual Stimuli on CRT", Mar. 1982, vol. BME–29, No. 3, pp. 184–192, New York.

By K. Plattig, "Gustatory and Olfactory Evoked Potentials In Man", 1987, vol. 2, pp. 961–962.

Primary Examiner—Angela D. Sykes
Attorney, Agent, or Firm—Young & Thompson

[57] ABSTRACT

Apparatus for use in the determination of the condition of the vegetative part of the nervous system and/or of sensory functions of an organism, i.e. a human being or animal. The apparatus comprises devices for generating and supplying to said organism at least one sensory stimulus chosen from a group of sensory stimuli, such as visual, sound, olfactory, gustatory, tactile or pain stimuli, and devices for measuring the skin potential and the evoked response of the organism to a stimulus. The measured data are processed by processing devices for automatically controlling the supply of at least one stimulus for providing a non-rhythmical sequence of stimuli. Preferably, pairs of stimuli are supplied for developing a conditioned reflex.

20 Claims, 1 Drawing Sheet

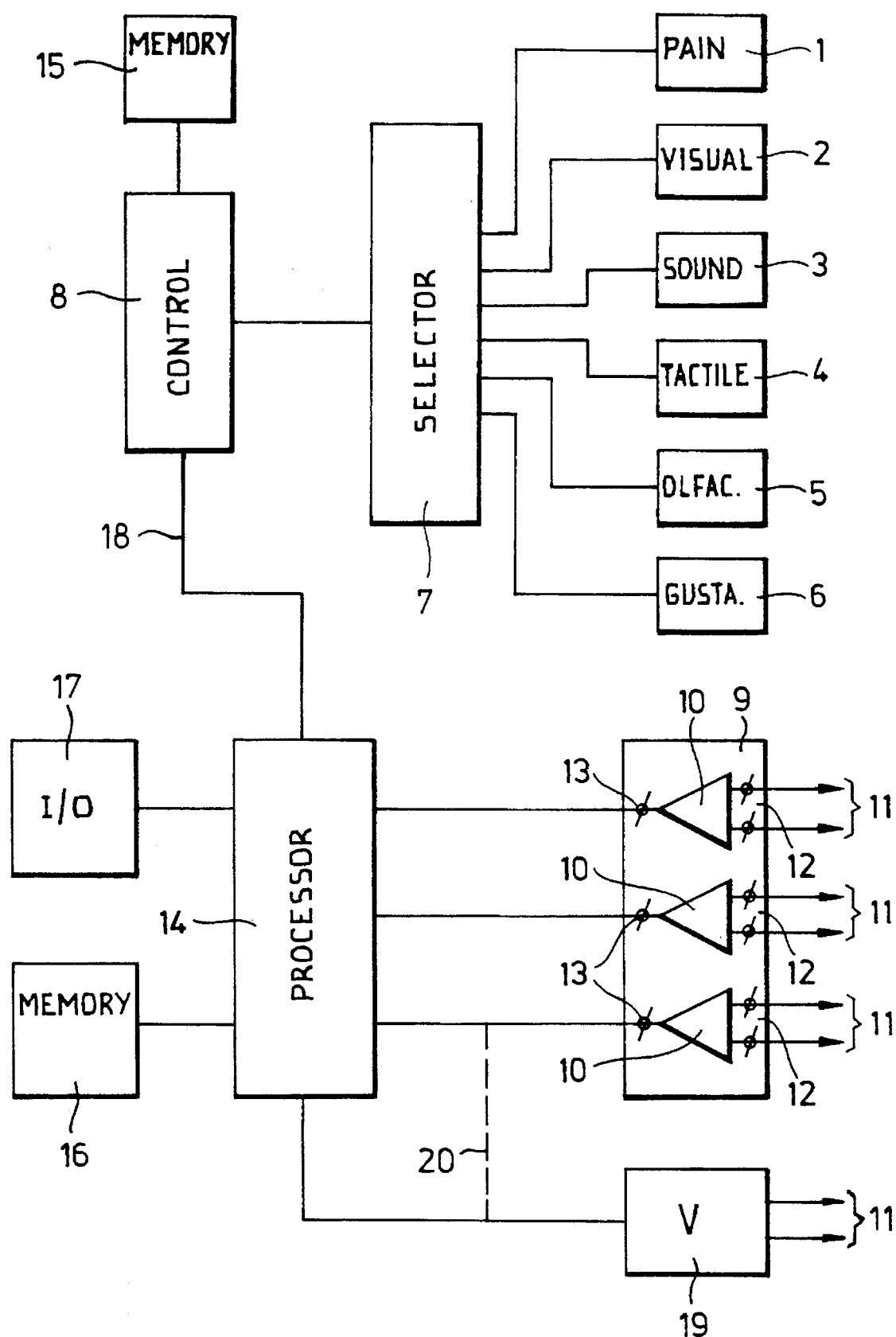

5,522,386

APPARATUS PARTICULARLY FOR USE IN THE DETERMINATION OF THE CONDITION OF THE VEGETATIVE PART OF THE NERVOUS SYSTEM

FIELD OF THE INVENTION

The invention relates to an apparatus for use in the determination of the condition of the vegetative part of the nervous system and/or of sensory functions of an organism, i.e. a human being or animal, comprising:
  means for measuring the skin or organ surface potential of the organism;
  means for generating and supplying to the organism at least one sensory stimulus chosen from a group of sensory stimuli;
  means for measuring the evoked response of the organism to the at least one sensory stimulus, and
  processing means, for processing the skin or organ surface potential and the evoked response values measured by the measuring means.

BACKGROUND OF THE INVENTION

Examination of the vegetative part of the nervous system or the sensory functions is carried out by supplying sensory stimuli to the organism under examination and by measuring the response to such a stimulus. The evoked response to a stimulus can be obtained from several variables of an organism, for example, skin potential, skin impedance, skin temperature, electrical signals from deep tissue e.g. muscle potentials, changes in the fluid production, e.g. the water production i.e. the water secretion or water content of tissue cells etc.

International patent application WO-A-9,014,749 discloses a method and an apparatus of the type mentioned above for analyzing neural sickness from the vegetative part of the nervous system of an organism, in response to sensory stimuli supplied to the organism under examination. Said stimuli can be chosen from a group of sensory stimuli, such as visual stimuli, sound stimuli, olfactory stimuli, gustatory stimuli, tactile stimuli or pain stimuli. The neural signals are achieved from measuring the evoked response of the organism to such a stimulus.

The results of said measurements can be evaluated and classified into different types, i.e. hypersympatheticotonia, pre-sympatheticotonia, vegetative normotonia (eutonia), preparasympatheticotonia and hyperparasympatheticotonia. By correlation of said types and other medical data, diagnosis on existing diseases or the probability of falling ill with a specific disease in future can be estimated.

International patent application PCT/NL91/00071, not a prior publication, discloses a method for measuring sensory functions of an organism, such as hearing, sight, smell, touch and pain, providing an objective assessment of the functioning of the sense organs, i.e. without the need for report by the organism under examination. In this method, specific stimuli are supplied to the organism, adapted to the sense under investigation i.e. auditory, visual, olfactory, gustatory, tactile, or pain stimuli. The reaction to such a specific stimulus is determined by measuring the evoked response of the organism.

It has been found that the evoked response by a sequence of stimuli of a certain type, e.g. light or sound, applied in a rhythmical manner is not stable over time. It is to say, as the time of stimulation increases, the response of the nervous system to said sequence of stimuli undesirable alters and/or decreases. Further, repeated investigation of the organs of sense, for example on the next day, can also have an adverse effect on the response of the organism to a specific stimulus or sequence of stimuli.

SUMMARY OF THE INVENTION

The invention now provides an improved apparatus for use in the determination of the condition of the vegetative part of the nervous system and/or of sensory functions of an organism, characterized by;
  control means, for controlling the supply of the at least one stimulus in terms of its' type, intensity, duration and/or repetition rate subject to the skin or organ surface potential and the evoked response values measured by said measuring means and processed by said processing means, for automatically providing a non-rhythmical sequence of stimuli.

With the apparatus according to the invention the vegetative nervous system and/or sensory functions of an organism, i.e. a human being or an animal, can be examined, wherein the evoked response of the nervous system to a sequence of stimuli is essentially independent over time providing reliable, satisfactory results. For example, compared to a rhythmical, repeatedly applied sequence of stimuli, an improvement in the accuracy of the determination of the condition of the vegetative part of the nervous system of a factor 3 to 5 is obtained. The stimulation pattern is automatically selected and controlled by the individual state of the vegetative nervous system of the organism, by analysis of the measured skin or organ surface potential of the organism.

It is noted that many different apparatuses for providing stimuli to an organism are known in the state of the art.

U.S. Pat. No. 4,131,113 discloses means for examining the human eye by analysis of electrical signals generated by the retinal of an eye in response to a quasi-random light stimulus. The stimulus applied is a bend-limited white-noise light intensity signal, projected onto the human eye through a cup electrode. However, the band-limited white-noise generator disclosed is not equipped for providing a controllable non-rhythmical sequence of stimuli, having adjustable parameters such as duration, intensity, repetition rate etc. Automatically controlling the sequence of stimuli subject to the state of the vegetative part of the nervous system of the organism is not disclosed nor suggested.

In a publication by Y. Kosugi et al. "Quantitative Evaluation of Saccadic Eye Movement Disorders Under Random Visual Stimuli on CRT" in IEEE Transactions on Biomedical Engineering, Vol. BME 29, no. 3. March 1982 a computer aided examination system is presented, in which a pseudo-random binary sequence is used for moving a target on a screen, in order to evoke saccadic eye movements. Controlling the supplied stimuli in terms of type, intensity, duration and repetition rate, subject to the state of the vegetative part of the nervous system and the evoked response of the organism is not described nor suggested.

U.S. Pat. No. 4,570,640 discloses an apparatus for monitoring the sensory system of a patient to enable determination of the level and depth of spinal and epidural nerve blocks affecting the sympathetic and motor nervous system. An electric stimulator is provided which can be manually or automatically activated. By comparing the response due to an applied stimulus against the response obtained from a reference level, the strength of the stimulus is controlled by not exceeding a too strong sensation and/or for gradually increasing the response in strength.

For the purpose of the present application, this apparatus lacks the feature of supplying a non-rhythmical sequence of stimuli, whereas the control means are not arranged for automatically controlling the stimulus in terms of its type, intensity, duration and/or repetition rate subject to the condition of the vegetative part of the nervous system and the processed measured values.

U.S. Pat. No. 4,201,224 discloses a method and apparatus for evaluating the state of the different regions of the human brain, for the purpose of diagnoses of the locus and extend of damage, impairment of brain functions etc. Although this apparatus is capable of providing random pain, light and sound stimuli, either alone or in combination, controlled by a microprocessor, the apparatus proposed is not arranged for automatically controlling the supply of the stimuli dependent on the vegetative part of the nervous system according to the apparatus of the invention.

In an embodiment of the invention, the processing means are arranged for determining the average value of the skin or organ surface potential in terms of DC and AC parameters, measured without a stimulus being supplied.

Dependent on the average value of the skin potential and the fluctuation or oscillation superpositioned thereon, the condition of the vegetative part of the nervous system of the organism can be suitable categorized in the types mentioned, i.e.:

I. HYPERSYMPATHETICOTONIA:

This type is characterized by the absence of background activity oscillations (up to 0.25 mV), stimuli do not evoke any responding reaction.

II. PRE-SYMPATHETICOTONIA:

Background activity is almost absent as well (up to 0.25 mV) but responsive reaction to stimuli is distinctly revealed (0.5 mV and higher).

III. VEGETATIVE NORMOTONIA (EUTONIA):

Background activity is recorded, amplitude being from 0.25 to 1 mV. Responding reaction to stimuli is distinct (0.5 mV and higher).

IV. PREPARASYMPATHETICOTONIA:

Background activity is marked (1–2 mV), responsive reaction to stimuli is distinct (1 mV and higher).

V. HYPERPARASYMPATHETICOTONIA:

Background activity is high (2–5 mV), responsive reaction to stimuli is distinct (1 mV and higher).

Spontaneous oscillations of the potential types III, IV and V are, as a rule, two-phase, sometimes single-phase (more often negative) deviations from an isoelectric line with frequency of 4–22 oscillations a minute. These oscillations are of different voltage, relatively rhythmic, sometimes in groups.

Obtaining the evoked response from measuring the skin or organ surface potential, the measurements may be recorded from fingers and toes, from the palmary sides of the hands and feet or from other parts of the skin of the body, or from the surface of the organs that can be reached by electrodes. If possible symmetrically from the right and the left part from the body or many regions of the body.

The active electrodes can be placed in the palmary side of the fingers and toes, right and left. The active electrodes can be placed also on any electro-active points of the skin or organs that can be reached. The passive electrodes can be placed on electrical low-active parts of the body. The registration of the potentials can be made from one point, two symmetrical points, from hands and feet at the same time or from combinations of some electro-active points of the skin or surface of organs that can be reached by electrodes, so that registration can be made polygraphical. This kind of examination is called elektrovegetography (EVG).

Under normal persons, in 6% of the cases the first type was found (hypersympatheticotonia), in 31.5% the second type (prosympatheticotonia), in 39.6% cases type III (vegetative normotonia), in 18.8% type IV (preperasympatheticotonia) and in 4% type V (hyperparasympatheticotonia). Thus the extreme types I and V were found in 10% of the patients. For further details, reference is made to the above-mentioned international application WO-A-9,014,794.

In the cause of any investigation of the condition of the vegetative part of the nervous system and/or sensory functions of an organism, a skin reflex may be lost due to habituation or adaptation.

Habituation or adaptation of the organism to a stimulus, e.g. its' type, intensity, duration and/or repetition rate, causing the results also to become unreliable. This applies both in the determination of the condition of the vegetative part of the nervous system of an organism as well as in measuring sensory functions of an organism by subjecting the organism to sequences of specific stimuli.

This problem can be solved by the development of a so-called conditioned reflex, in which habituation to a first stimulation is prevented by applying another, second stimulation. For example, a stimulus of the same type, but of different intensity or duration, or a stimulus of a different type. In order to stabilize the response of the organism to the stimuli supplied, i.e. preventing the results to become unreliable, this other stimulus has to provoke an emotional type response of the organism. Suitable stimuli for this purpose are stimuli which are experienced as unpleasant, for example pair, loud noises, bright light flashes, certain words or phrases, etc.

In a yet further embodiment of the apparatus according to the invention, the processing means are arranged for detecting habituation or adaptation of the organism to the sensory stimuli supplied by analyzing the measured evoked response. It has been found that a state of habituation adaptation can be determined by detecting a decrease in the applitude of the measured evoked response, below a certain, predetermined level.

In a yet further embodiment of the apparatus according to the invention, the control means are arranged for providing a first and second stimulus chosen from a group of sensory stimuli, the second stimulus provoking an emotional type response, its' type, intensity, duration and/or repetition rate being subject to the determined state of the vegetative nervous system and the detected habituation or adaptation of the organism to the first stimulus, by analyzing the amplitude of the measured evoked response.

This embodiment of the apparatus is based on the principle of stimulation of the emotional vegetative system. This stimulation has a feedback character. The organism itself, depending on its state of the vegetative nervous system "dictates" the stimulation pattern of the device, i.e. in terms of its type, intensity, duration and/or repetition rate. For obtaining reliable results it is very important to determine the condition of the vegetative part of the nervous system of the organism under examination, in order to make a justified selection of the stimuli for inducing a conditioned reflex.

In applying the apparatus according to the invention for the determination of the condition of sensory functions of an organism, the control means are arranged for providing a first stimulus chosen from a group of sensory stimuli, adapted to the sensory function of the organism to be examined. Its' intensity, duration, frequency etc, being controllable subject to the sensory function to be examined. This kind of examination is, also called electrosensometry and can be carried out as follows, for example.

Potentials of the phalanxes of the hand or foot or from other electroactive points are recorded. The active electrode is fixed on the palm surface, the inner side of the phalanx or another electroactive point, and the passive electrode is fixed on the back surface of the phalanx or an other, less electroactive point. Then one or more sensory stimuli are applied, and each time potential changes are recorded afterwards. The results of the measurements are processed.

If the skin potential changes upon repeated (2–3 times) sound stimulation, this means that the sense of hearing perceives the sound stimulus. In repeated investigation it is possible to determine the threshold value of the sound perception on the basis of the intensity of the stimulus. If the skin potential changes upon repeated (2–3 times) light stimulation, this means that the sense of vision perceives this light stimulus. In repeated investigation it is possible again to determine the threshold value of light perception on the basis of the intensity of the stimulus. Using the same principle, the visual field, optionally dependent on the visual angle, can be investigated.

If the skin potential changes upon repeated (2–3 times) olfactory stimulation, this means that the sense of smell perceives the olfactory stimulus given. The limits of perception of olfactory stimuli can be determined by repeated examination on the basis of the intensity of the stimulus. If the skin potential changes upon repeated (2–3 times) tactile stimulation, this means that the tactile sense is preserved in the area concerned. When a moderate prick with a needle or a special bristle causes a change in the skin potential, this shows that the patient has experienced a pain sensation.

The results of examination are objectified by recording the cutaneogalvanic reaction instead of the subjective reports or in combination with such subjective reports.

However, when the examination of the tactile sense, for example, is repeated 5 to 10 times the response in the form of a potential change dies away as a result of the phenomenon of habituation.

For inducing a conditioned reflex with a second stimulus, particularly an electrical stimulus, two small electrodes (for example 1 cm$^2$) are connected to the palm and the back surface of a finger of the other hand or on an other area, and combinations of stimuli of the sense under investigation with the second stimulation are applied. This other stimulation is preferably an electric pain stimulation that may be of short duration (0,5–2) seconds), with an intensity of slightly above the pain threshold value of the organism. This electric stimulation is applied 1–2 seconds after applying the specific stimulus and after for example 10–15 seconds such a combination of stimuli is repeated. After several of such combinations, for example 3–5, a stable conditioned cuteogalvanic reflex is developed and under these conditions the threshold of the sensitivity of the senses investigated is determined correctly in 93–95% of the cases. The second stimulation is preferably applied with irregular intervals and with an irregular intensity. An application in pairs of for example an electric and a visual stimulus is also advantagous.

In case a conditioned reflex to a pain sensation was developed, the results of the investigation of the sensory functions turned out to be positive in more than 90 percent of the cases. The apparatus can be used to separately examine the organs of sense, where appropiate, on both sides (right and left), optionally as a function of the direction, giving a very important contribution to the topical diagnosis of diseases and defects. The apparatus according to the invention is applicable with living beings disposing of senses, primarily man; and is of special interest in the examination of young children and new born infants. Electrosensometry can also be used in veterinary medicine when examining the senses of animals, in particular pets and farm animals.

In the most simple embodiment of the apparatus according to the invention, the non-rhythmical sequence of stimuli consist of stimuli of one type, for example adapted to a sensory function to be examined such as pain, light or sound stimuli, the intensity, duration, repetition rate etc. of which being non-rhythmical altered during the time of stimulating, such that no habituation to a certain form of stimulus will occur.

However, it has been found that for determining the condition of the vegetative part of the nervous system an even more accurate measurement can be obtained with a further embodiment of the apparatus according to the invention, wherein the supply means comprise several stimulus generators for supplying sensory stimuli of a mutually different type, the control means being arranged for providing an arbitrary sequence of stimuli of different type.

Although stimuli of different type can be supplied simultaneously, a yet further embodiment of the apparatus according to the invention comprises selector means connected to the control means and stimulus generators, for providing one type of stimulus at a time. This has the advantage that the response to a certain type of stimulus can be uniquely determined.

Very promising results in inducing a conditioned reflex have been obtained from sequences composed of pairs of stimuli of mutually different type, e.g. a pain and light stimulus, either applied simultaneously or subsequently.

The non-rhythmicity of the sequence may be obtained by providing during a certain time period pairs of stimuli, and during a subsequent time period stimuli of the one and/or other type alone. During these time periods, the stimuli itself may be supplied periodically or rhythmically. Important is that the sequence as a whole has a non-rhythmical character.

From the control point of view, for supplying a pain stimulus, an electrical generator having means for supplying an adjustable electrical signal above the pain threshold of an organism is advantageous. The output signal of the electrical generator can be adequately adjusted with respect to its amplitude, frequency, polarity, repetition rate etc.

Further embodiments of the apparatus according to the invention may comprise adjustable optical signal generator means, such as an incandescent lamp for providing controllable light flashes or, for example, a video monitor for showing pictures in order to generate an emotional response or the like.

Further, adjustable sound generator means may be provided, for supplying an audible tone signal adjustable in intensity, frequency and duration, or a voice generator or the like, for generating an emotional response to certain words of phrases.

Further embodiments of the apparatus according to the invention may comprise means for supplying a selective tactile, olfactory or gustatory stimulus to an organism. Means suitable for this purpose are known in practice. Reference is made to K. Plattig "Gustatory and Olfactory Evoked Potentials by Man", published in Proceedings of the 9th Annual Conference of the IEEE Engineering in Medicine and Biology Society, Part 2, Nov. 16, 1987, pages 961–962.

In an embodiment of the apparatus according to the invention, the measuring means are arranged for measuring at least one electrical variable of the skin and/or an organ of the organism, for example skin impedance or skin potential, via electrodes to be applied on the skin and/or the surface of an organ that can be reached by electrodes (stomach, mouth etc.), comprising at least one amplifier having a pair of electrodes for application to the skin or the surface of an organ, this at least one amplifier having a time constant of 1 sec or higher; up till DC. The registration of the electrical variable can be made from one point, two symmetrical points, from hands and feet at the same time or from a combination of electro-active points of the skin or surface of organs that can be reached by electrodes.

Amplifiers suitable for measuring the skin or organ surface potential are known in practice. It has been found that an amplifier having a time constant of about 3 sec, with which it is possible to register three or more electrical potential waves/min., provides very accurate results for determining the condition of the vegetative part of the nervous system in applying different kind of stimuli.

In order to uniquely determine the response to a specific stimulus, it is preferred, in a further embodiment of the apparatus according to the invention, to have the generator means and measuring means cooperatively interconnected.

In a further embodiment of the apparatus according to the invention, at least one voltmeter means is provided for measuring the skin or organ surface potential of the organism. By using a DC voltmeter the background level of the skin or organ surface potential without a stimulus being applied can be measured. In case of a DC amplifier the voltmeter means may be connected to measure the output signal of the amplifier.

In yet a further embodiment, for measuring the evoked response, the amplifier comprises means for compensating the background level of the skin or organ surface potential, in order to enhance the measurement accuracy.

For processing the measured potential waveforms with respect to their shape, rise and fall times, mono- or biphase, power content, etc., a waveform analysing means and/or recording means for recording measured electrical signals may be provided, known as such.

For analyzing the measured data, the processing means may comprise analog or digital filter means. With these filter means the AC component of the skin potential or organ surface potential can be analyzed, such to determine the stae of the vegetative part of the nervous system.

For determining adaptation of the organism to the sensory stimuli supplied, preferably analog or digital peak value detecting means may be provided, coupled to or incorporate in the processing means. Whenever, the amplitude of the evoked response drops below a certain level, related to the DC background level of the type of the condition of the vegetative part of the nervous system mentioned, the sequence of stimuli is automatically adapted, in order to develop a stable skin potential during examination.

In the preferred embodiment of the apparatus according to the invention, the processing means and the control means comprise a programmable computer means, having memory means, for processing the measured values and controlling a certain sequence of stimuli to be supplied to an organism, respectively. These computer means, may be advantageously combined into one processor, for example a microprocessor.

With a suitable programming of the computer processing means, measured data can be processed to present medical data to be used in making a diagnosis by a physician, for example. For this purpose means such as a display, printer etc. may be coupled to or provided with the processing means. Preferably means are provided, such as a keyboard, card reader, disk reader etc. for entering medical data or medical related data of the organism under examination, used in processing the measured data.

When using computer means, the measured values may be processed using suitable analyzing techniques, such as Fourier analysis, correlation techniques, statistical analysis etc. known in practice.

BRIEF DESCRIPTION OF THE DRAWINGS

The apparatus according to the invention will now be explained in more detail in conjunction with the accompanied drawing, which shows a block circuit diagram.

DETAILED DESCRIPTION OF THE EMBODIMENT

In the block circuit diagram of the preferred embodiment of the apparatus according to the invention, the reference numerals 1–6 denote stimulus generators, i.e. a pain stimulus generator 1, a visual stimulus generator 2, a sound stimulus generator 3, a tactile stimulus generator 4, an olfactory stimulus generator 5 and a gustatory stimulus generator 6. These stimulus generators are connected to a selector means 7, which is internally connected to a control means 8, for example a programmable computer. Controlled by the computer, the control means 8 can select a specific stimulus generator 1–6, to provide a non-rhythmical sequence of sensory stimuli, for example a programmed non-rhythmical sequence of stimuli.

For measuring the evoked response of the nervous system of an organism under examination, a measuring device 9 is obtained, having a plurality of amplifiers 10, each of which having a pair of electrodes 11 connected to its input 12, whereas their outputs 13 are connected to a processing means 14. The amplifiers 10 can be of the a type used for medical measurements, having a time constant of 1 sec or higher, preferably up till DC. The electrodes 11 are of a known type for recording surface potentials of the skin or organs that can be reached by electrodes (stomach, mouth etc.). The electrodes, for measuring the skin potential, can be placed in the palmar side of the fingers and toes, right and left, or other suitable parts of, for example, the human body, such as disclosed in the international application WO-A-9,014,794, and the international application PCT/NL91/00071. The amplifiers 10 are preferably provided with means for compensating the background level of the skin or organ surface potential, i.e. the potential level of the skin or organ surface without a stimulus being applied.

The processing means 14 may comprise in its simplest form one or more voltmeters, filter means, i.e. analog or digital filter means, and amplitude measuring means, such as analog or digital peak value detecting means, known in practice. In a further developed embodiment a waveform analyzer may be provided, for analyzing the electrical potential waves measured. For recording these waves, recording means in the form of a paperchart recorder, for example, may be provided. In a sophisticated embodiment of the apparatus according to the invention, the processing means 14 may comprise a computer for analyzing the potential waveforms obtained, i.e. the background level and the waveforms related to the vegetative part of the nervous system and the measured data due to an applied sequence of stimuli.

In order to automatically control the control means 8 and to uniquely determine the response to a specific stimulus, e.g. a pain or sound stimulus, the processing means 14 is connected to the control means 8, as indicated by line 18.

The computer in the control means 8 and the processing means 14 is provided with memory means 15 and 16, respectively, such as Random Access Memory (RAM), Read Only Memory (ROM) etc. In these meories an algorithm for controlling and processing is stored, whereas the processed and other related data may be stored in these memories. The computer in the control means 8 and the processing means 14 may be combined into one single device, for example a microprocessor. Microprocessors and memory means suitable for use in the apparatus according to the invention are known in practice.

For presenting processed data and/or entering data related to the organism under examination, input/output means 17, are connected to the processing means 14. Such as a keyboard, a disk or card reader device and/or a video monitor or printer, etc.

In some cases it is advantageous to have separate voltmeter means 19 having electrodes 11 for measuring the skin or organ surface potential of an organism, connected to the processing means 14. These voltmeter means 14 may be connected to the output of an amplifier 10, i.e. a DC amplifier 10, indicated by broken line 20.

Although certain types of pain stimuli can be given to an organism under examination, it is preferred to use an electrical generator, having active electrodes to be placed on the skin surface, for example, of an organism under examination, and capable of generating an electric voltage or current signal above the pain threshold of the organism. It is advantageously to use an electrical generator, for example a pulse generator, because the parameters of the generated electric signal, for example the pulse width, pulse height, pulse duration, polarity, pulse repetition rate etc. can be relatively easily and automatically adjusted. For the purpose of the present invention, a pulse generator capable of generating pulses having an adjustable amplitude, an adjustable pulse repetition rate and an adjustable pulse duration suffices.

The visual stimulus generator 2 can be comprised of an incandescent lamp of 0–100 W, coupled to controllable power supply means for providing light flashes. In a sophisticated embodiment, the visual stimulus generator means 2 may comprise video monitor means for displaying pictures for providing an emotional stimulus.

The sound stimulus generator means 3 may comprise a tone generator, for generating a tone in the audible frequency range with an adjustable strength above the threshold of audibility and below the pain threshold of audibility. For the purpose of the present invention, the tone generator must also be capable of providing tone bursts of controllable duration.

The sound stimulus generator 3 may also comprise a voice generator or means for providing voice sound, in order to provoke an emotional type response of the nervous system on hearing certain words or phrases.

The tactile stimulus generator 4 is a means for providing tactile stimuli to, for example, the skin of an organism.

The olfactory stimulus generator 5 is a means for providing an olfactory stimulus derived from different olfactory substances, such as camphora, eau de cologne etc. The gustatory stimulus generator 6 is a means for providing a gustatory stimulus by applying a sweet, acid, bitter or substance of other flavouring to an organism under examination.

The control means 8 may be arranged such that, according to the present invention, an arbitrary non-rhythmical sequence of stimuli of one type or an arbitrary non-rhythmical sequence of stimuli of different kind can be applied. These stimuli may vary in intensity, duration, repetition rate etc., as described.

With the apparatus according to the invention, called electrovegetograph or elektrosensometer, an accurate determination of the condition of the vegetative part of the nervous system of an organism and/or of sensory functions can be obtained. The resultant measurements, such as electrovegetograms (EVG), can be used in many disciplines of medicine for diagnostic and/or prognostic purposes.

It will be evident to a person skilled in the art, that the invention is not limited to the embodiment described or to an embodiment using all types of stimulus generators disclosed. Further, the measuring means may comprise more or less amplifiers 10 for measuring skin or organ surface potential waves, or may be substituted or enhanced by means for measuring other electrical parameters of the skin, for example skin conductivity, temperature, etc.

I claim:

1. Apparatus for use in the determination of the condition of the vegetative part of the nervous system and/or of sensory functions of an organism, comprising:

first means for measuring the skin or organ surface potential of the organism;

means for generating and supplying to the organism at least one sensory stimulus selected from the group consisting of pain, visual, sound, tactile, olfactory and gustatory, and second means for measuring the evoked response of the organism to the at least one sensory stimulus, processing means for processing the skin or organ surface potential and the evoked response values measured by the measuring means, and control means operating independently of the second means for measuring the evoked response, said control means controlling the supply of the at least one stimulus in terms of its type, intensity, duration and/or repetition rate subject to the skin or organ surface potential and the evoked response values measured by said first and second measuring means and processed by said processing means, for automatically providing a non-rhythmical sequence of stimuli.

2. Apparatus according to claim 1, wherein the processing means are arranged for determining the condition of the vegetative nervous system by ascertaining the average value of the skin or organ surface potential in terms of DC and AC parameters, measured without a stimulus being supplied.

3. Apparatus according to claim 2, wherein the processing means are arranged for detecting habituation or adaptation of the organism to the sensory stimuli supplied by analyzing the amplitude of the measured evoked response.

4. Apparatus according to claim 3, wherein the control means are arranged for providing a first and second stimulus selected from said group of sensory stimuli, the second stimulus provoking an emotional type response, its type, intensity, duration and/or repetition rate being subject to the determined condition of the vegetative nervous system and the detected habituation or adaptation of the organism to the first stimulus.

5. Apparatus according to claim 4, wherein the first stimulus is adapted to a sensory function of the organism.

6. Apparatus according to claim 3, wherein the processing means comprise analog or digital peak value detecting means for detecting a decrease in the amplitude of the measured evoked response, below a certain, predetermined level.

7. Apparatus according to claim 1, wherein the processing means comprise analog or digital filter means for analyzing the measured skin or organ surface potential.

8. Apparatus according to claim 1, wherein the processing means comprise waveform analyzing means.

9. Apparatus according to claim 1, wherein the processing means and the control means (8) comprise programmable computer means having memory means (15,16) for processing the measured values and controlling the sequence of stimuli to be supplied to the organism.

10. Apparatus according to claim 1, wherein the first means for measuring the skin or organ surface potential of the organism comprise DC voltmeter means.

11. Apparatus according to claim 1, wherein the first measuring means for measuring the skin or organ surface potential and the second means for measuring the evoked response of the organism comprise at least one amplifier having a pair of electrodes for application to the skin or the surface of an organ, the at least one amplifier having a time constant of 1 sec or higher.

12. Apparatus according to claim 11, wherein the at least one amplifier is a DC amplifier.

13. Apparatus according to claim 11, wherein the at least one amplifier comprises means for compensating the background level of the skin or organ surface potential.

14. Apparatus according to claim 1, wherein the first measuring means comprise recording means for recording measured electric signals.

15. Apparatus according to claim 1, wherein the means for generating and supplying at least one sensory stimulus comprise several stimulus generators for supplying sensory stimuli of a mutually different type, the control means being arranged for providing a non-rhythmical arbitrary sequence of stimuli of different type.

16. Apparatus according to claim 15, wherein the control means are arranged for providing pairs of stimuli of mutually different type.

17. Apparatus according to claim 1, comprising at least one electrical generator, having means for supplying an adjustable electrical signal above the pain threshold of the organism, and at least one optical signal generator, having means for supplying an adjustable optical signal to the organism, and at least one sound generator, having means for supplying an adjustable sound signal to the organism, and means for supplying an adjustable, selective tactile stimulus to the organism, and means for supplying an adjustable, selective olfactory stimulus to the organism, and means for supplying an adjustable, selective gustatory stimulus to the organism.

18. Apparatus according to claim 1, wherein the stimulus generating means and processing means are cooperatively interconnected, in order to uniquely determine the response to a specific stimulus.

19. Apparatus according to claim 1, wherein the processing means comprise means for presenting processed measured data relating to a medical condition of the organism under examination.

20. Apparatus according to claim 1, wherein the processing means comprise means for inputting, data relating to a medical condition of the organism under examination.

* * * * *